United States Patent
Califorrniaa

(10) Patent No.: US 7,121,998 B1
(45) Date of Patent: Oct. 17, 2006

(54) VENTED MICROCRADLE FOR PRENIDIAL INCUBATOR

(76) Inventor: Eurica Califorrniaa, P.O. Box 2328, Malibu, CA (US) 90265-7328

( * ) Notice: Subject to any disclaimer, the term of this patent is extended or adjusted under 35 U.S.C. 154(b) by 0 days.

(21) Appl. No.: 10/908,861

(22) Filed: May 30, 2005

Related U.S. Application Data

(60) Provisional application No. 60/577,958, filed on Jun. 8, 2004.

(51) Int. Cl.
 *A61D 7/00* (2006.01)
(52) U.S. Cl. .......................... 600/33; 600/22
(58) Field of Classification Search ........... 600/33–35, 600/21–22; 128/897–898; 435/7.2, 29, 435/366, 373, 374, 325, 288.4, 288.5, 297.5, 435/305.2, 305.3
See application file for complete search history.

(56) References Cited

U.S. PATENT DOCUMENTS

| | | | |
|---|---|---|---|
| 4,574,000 | A | 3/1986 | Hunter |
| 6,193,647 | B1 | 2/2001 | Beebe et al. ................. 600/33 |
| 6,448,069 | B1 | 9/2002 | Cecchi et al. ............ 435/305.2 |
| 6,488,872 | B1 | 12/2002 | Beebe et al. |
| 6,673,008 | B1 | 1/2004 | Thompson et al. ........... 600/33 |
| 6,694,175 | B1 | 2/2004 | Califorrniaa ................ 600/474 |
| 6,695,765 | B1 | 2/2004 | Beebe et al. |
| 6,787,324 | B1 | 9/2004 | Jordan et al. ................ 435/7.9 |

| | | | |
|---|---|---|---|
| 2002/0068358 | A1 | 6/2002 | Campbell et al. ........ 435/289.1 |

OTHER PUBLICATIONS

Califorrniaa E. Thermoregulation of human embryos and hatchlings in a prenidial incubator using infrared microthermography. Trends in Reproductive Biology. 2005;1:63-67.

Cone T.E. Jr. History of the care and feeding of the premature infant. Boston: Little, Brown, 1985. pp. 21-22.

Ok J., Chu M., and Kim C.-J. Pneumatically driven microcage for micro-objects in biological liquid. Proc. IEEE Conf. Micro Electro Mechanical Systems (MEMS '99), Orlando, FL, Jan. 1999, pp. 459-463.

Roux C., Joanne C., Agnani G., Fromm M., Clavequin M.C., and Bresson J.L. Morphometric parameters of living human in-vitro fertilization embryos; importance of the asynchronous division process. Human Reproduction. 1995;10:1201-1207.

Suh R.S., Phadke N., Ohl D.A., Takayama S., Smith G.D. Rethinking gamete/embryo isolation and culture with microfluidics. Human Reproduction Update. 2003;9:451-61.

(Continued)

*Primary Examiner*—John P. Lacyk

(57) ABSTRACT

A vented microcradle comprising a microfabricated enclosure designed to maintain a human embryo or hatching in a controlled care environment, the enclosure forming a cradle support for the human embryo or hatchling and having a ventilation system to provide the human embryo or hatchling with gentle fluidic ventilation via associated microfluidics. In a preferred embodiment, the microfabricated enclosure is a picket fence structure with a vented flooring; the vented flooring, which has a grill-like pattern, forms part of the ventilation system in connection with associated microfluidics.

22 Claims, 5 Drawing Sheets

OTHER PUBLICATIONS

Silverman W.A. Incubator-baby side shows. Pediatrics. 1979;64:127-141.

Cragin E.B. The Sloane Hospital incubator. Journal of the American Medical Association. 1914;63:947.

De Vos A., Van Steirteghem A. Zona hardening, zona drilling and assisted hatching: new achievements in assisted reproduction. Cells Tissues Organs. 2000;166:220-7.

Shiloh H., Lahav-Baratz S., Koifman M., Ishai D., Bidder D., Weiner-Meganzi Z., Dimfeld M. The impact of cigarette smoking on zona pellucida thickness of oocytes and embryos prior to transfer into the uterine cavity. Human Reproduction. 2004;19:157-9.

Pelletier C., Keefe D.L., Trimarchi J.R. Noninvasive polarized light microscopy quantitatively distinguishes the multilaminar structure of the zona pellucida of living human eggs and embryos. Fertility and Sterility. 2004;81 Suppl 1:850-6.

Brown A., George R. The care and feeding of the premature infant. Archives of Pediatrics. 1917;34:609-616.

Hess J.H. Premature and Congenitally Diseased Infants. Ch. IX: Incubators. Philadelphia and New York: Lea & Febiger, 1922.

(Thompson et al. US 6,673,008)

(Beebe et al. US 6,193,647)

(Cecchi et al. US 6,448,069)

(Cecchi et al. US 6,448,069)

(Cecchi et al. US 6,448,069)

(Beebe et al. US 6,193,647)

VENTED MICROCRADLE FOR PRENIDIAL INCUBATOR

BACKGROUND

1. Field of the Invention

My invention relates to a vented microcradle for use in an incubator system specifically designed to maintain a premature infant in a controlled care environment from creation to implantation. The incubator system is thus an engineered environment specifically designed for the care of human embryos and hatchlings. The engineered environment is preferably a micro intensive care unit (μICU). My invention is intended for intimate combination with my teaching in U.S. Pat. No. 6,694,175 for a "Method of monitoring the body temperature of human embryos and hatchlings", which historically is the first patent for pre-implantation patient care to be classified under incubators for premature infants (current U.S. class/subclass 600/22).

A human is an embryo only from conception to hatching. Hatching is an event that takes place when an embryo escapes the shell of the egg that he or she was conceived in. A human is a hatchling only from hatching until implantation (nidation).

A number of authorities still persist in using certain terms in an incorrect fashion, due in part to ignorance about the human hatching event. This circumstance requires one to be especially discerning in considering prior art uses of various terms (e.g., embryo).

A human embryo or hatchling is a prenid ("PRE-nid"), which means a prenidial ("pre-NID-e-al") infant; thus, an infant is a prenid up to implantation. The term prenid is especially convenient because it encompasses both human embryos and hatchlings. The word prenid is derived by shortening of pre-nidation, which means pre-implantation, and the word prenidial is the adjectival form. To clarify this etymology, note that the nidus ("NID-us"), Latin for nest, refers to the uterine cavity; hence, prenidal ("pre-NIGH-dal") means before the baby enters the uterine cavity, e.g., via the fallopian tube. In contrast, the nidia (from L. nidus, nest) is the settlement the baby makes at implantation (compare L. colonus, colonia), and so prenidial means before the baby implants, i.e., establishes a settlement in the nest.

Outside the maternal body, prenidial infants are premature infants because it is premature for them to be outside the maternal body on their own. Prenidial gestation refers to a maternal, bodily provision for prenidial development as well as to prenidial developmental needs in general, whereas prenidial incubation refers to an engineered provision for development outside the maternal body in a manner analogous to natural gestation. Thus, sophisticated incubator systems for premature infants prior to implantation are termed prenidial incubators. Prenidial incubators are like neonatal incubators, except their technology pertains to patient care before implantation. Hence, my invention relates to a vented microcradle for a prenidial incubator.

Technically speaking, "in vitro fertilization" refers only to the event or act of fertilization taking place in vitro, and not to subsequent care. In contrast, the whole practice of caring for the baby up to implantation, whether inside or outside the maternal body, is termed prenidial medicine, and care outside the maternal body is termed prenidial incubation. A prenidial incubator is required for care prior to transfer for children created by in vitro fertilization.

But even apart from in vitro fertilization, prenidial incubators find use whenever a baby needs to be taken from the maternal body and transferred to a prenidial incubator. For example, technology is under development that will eventually enable us to readily detect a prenid within the maternal body. U.S. Pat. No. 6,787,324 (Jordan et al.) for a "Method and apparatus for detecting conception in animals" is noted as an example of emerging veterinary and human medical research in this direction. Thus, if the mother dies in a traffic accident for example, then upon detection her baby can be transferred to a prenidial incubator for care while awaiting transfer to an adoptive mother. Similarly, if for example the mother's fallopian tube is blocked and the baby is trapped, or for example if the mother requires treatments that cannot be safely done with the baby present, the baby might need to be temporarily transferred to a prenidial incubator and then either transferred back or transferred to a surrogate mother.

Early neonatal incubators suffered from a lack of fresh air because a patient's need for proper ventilation was not originally understood. As Alan Brown and Ruggles George report in the *Archives of Pediatrics* in 1917, "Absence of fresh air was a disadvantage in an enclosed incubator that even properly regulated heat did not outweigh." In a practical approach to the problem, Edwin B. Cragin reports in 1914 in the *Journal of the American Medical Association* on the use of "a small electric fan" in the Sloane Hospital incubator to maintain "a gentle current of filtered air passing through" the incubator. The technology of the vented microcradle is analogous in principle to that of a modern, ventilated neonatal enclosure, except that prenidial infants live in a fluid incubation medium whereas neonatal infants live in the air we breathe. Thus, when speaking of ventilation for a prenidial infant, one means a gentle flowing of the fluid incubation medium over the infant's egg (embryo stage) or body (hatchling stage) so as to refresh needed substances and remove wastes. Accordingly, fluidic ventilation is not to be confused with an air system for an incubator; but note however that in a prenidial incubator the air system may contribute to fluidic ventilation by way of influencing the chemical balance ($O_2$, $CO_2$, etc.) of the fluid incubation medium, e.g., the $CO_2$ content can influence pH.

2. Prior Art

During prenidial gestation infants live in a fluid medium, and then from implantation until birth infants live attached to the maternal body. Because prenidial infants live in a fluid medium and are of microscopic size, caring for them outside the maternal body involves different technologies than caring for premature infants in later development. Notably, prenidial incubation is now a rapidly evolving technology, inspired mainly by advances in integrated microfabrication technology (IMT). To make a comparison to the history of progress in the care of premature infants in neonatal development, early efforts of neonatal incubation faltered for failure to thermoregulate and ventilate the babies in a competent fashion. Sadly, the incubator care of premature infants in prenidial development faltered for the same reasons.

Fortunately, the modern art of prenidial incubation has been introduced by my teaching on the competent manner of thermoregulation in U.S. Pat. No. 6,694,175 for a "Method of monitoring the body temperature of human embryos and hatchlings" (incorporated here by way of reference). Prior to my teaching, practitioners of what was called in vitro fertilization failed to grasp the correct principles of thermoregulation, and so their crude, petri dish based incubator systems did not function competently; in a nutshell, they confused the temperature of the fluid incubation medium, in which prenidial infants are kept, with the infant's endogenous actual body temperature. In other words, they confused the temperature of the infant's environment with a measure of the infant's own body temperature. This problem of incompetent thermoregulation led to enormous infant mortality rates, particularly among infants being incubated in the later stages of prenidial development since these stages reflect increased endogenous heat production on the part of the infant. (Californiaa, E. Thermoregulation of human embryos and hatchlings in a prenidial incubator using infrared microthermography. Trends in Reproductive Biology. 2005;1:63–67.)

Of historical interest, pediatric historian Thomas E. Cone, Jr. notes that similar incompetence persisted during the early development of neonatal incubators, and, moreover, that it was an understanding and solution of this problem that prompted the modern age of neonatal care. (Cone, T. E., Jr. History of the Care and Feeding of the Premature Infant. Boston: Little, Brown, 1985. p. 21–22.) But rather than realizing their own incompetence, practitioners of in vitro fertilization simply attributed their shortcomings to "genetic causes" as opposed to environmental causes, even despite it being fairly well known that improper thermoregulation at this stage can induce a wide spectrum of gross chromosomal abnormalities, also known as cytogenetic abnormalities (e.g., aneuploidies).

My method in U.S. Pat. No. 6,694,175 solves the problem of incompetent thermoregulation. According to this method, the techniques of infrared microthermography are used to distinguish a baby's temperature from the temperature of the surrounding environment, and a feedback loop is used to maintain optimal temperature for the baby for the sake of proper thermoregulation. (Californiaa, E. Ibid.)

As stated above, in developing modern neonatal incubators, along with the most essential step of thermoregulation, another key step proved to be ventilation. By analogy, the need for similar progress in ventilation technology in the context of prenidial incubation forms the necessity of my present invention. Because neonates live in the air we breathe, neonatal ventilation is gas/vapor phase ventilation. In contrast, because prenids live in the fluid of the uterine tube and uterine cavity, prenidial ventilation is liquid phase ventilation.

Neonatal incubation differs from prenidial incubation in that neonates require ventilation for oxygen and humidity and to expel carbon dioxide whereas prenids also require ventilation for nourishment and other waste removal. In other words, neonates breathe air, are fed internally, and their diapers are changed, whereas prenids transfer all metabolic resources and wastes via the fluid medium in which they live submerged.

Hunter (U.S. Pat. No. 4,574,000—"Artificial fallopian tube") is a clear forerunner in appreciating the need for a human embryo or hatchling to experience fluidic ventilation in a fabricated device. He speaks of using a micropump to infuse a nutrient solution through an artificial (fallopian) tube to ensure that a fertilized "egg is provided with an adequate supply of fresh nutrient solution". (column 5, lines 38–50). The teaching of Thompson et al. in U.S. Pat. No. 6,673,008 for a "Fallopian tube and method of in vitro fertilization and embryo development" also appreciates the necessity of fluidic ventilation for prenidial development in likeness to the fluidic ventilation provided by the fallopian tube. In effect, Thompson et al. roughly mimic Hunter's approach with an externalized (as opposed to a prosthetic) device. But unlike Hunter's device, theirs is not a microfluidic device. As shown in FIG. 1, Thompson et al. rely on a well-type structure 1 with a microporous floor 2 to keep an embryo P ("P" for prenid) housed at the bottom of an enclosed tank 3. Campbell et al. in published application US 2002/0068358 also teach a well for housing an embryo. The teaching of Beebe et al. in U.S. Pat. No. 6,193,647 for a "Microfluidic embryo and/or oocyte handling device and method" somewhat appreciates the necessity of fluidic ventilation, however, their appreciation appears to be compromised by their objective of employing fluid flow to roll the eggs of embryos; consequently, the rate of fluid flow they suggest appears to be much too harsh. For given that (per Thompson et al.) the average velocity of an embryo along the length of the fallopian tube is roughly on the order of 0.2 micrometers per second, with fastest transit rates roughly on the order of 0.35 micrometers per second in portions of the fallopian tube, the fluid flow rates suggested by Beebe et al., with embryos traveling at a velocity of 187 to 250 micrometers per second for a fluid flow rate of 380 micrometers per second, appear to be excessive by several orders of magnitude. As shown in FIG. 2, Beebe et al. teach a channel-type structure for housing an embryo P. Beebe et al. also teach a well-type structure for housing an embryo.

IMT (integrated microfabrication technology) employs diverse arts to make small size systems and devices. IMT technology includes submillimeter, micrometer, and nanometer technologies, and often incorporates these with larger scale technologies. IMT designs offer important benefits such as intimate integration with electronic circuitry and the ability to manufacture arrays of designs on a single substrate. IMT arts especially relevant to this disclosure include micro electro mechanical systems (MEMS) technology and microfluidic technology. Note that microfluidic technology relates to fluid flow on a small scale and also includes micropump and microvalve technology.

A microcradle is a cradle engineered for a baby's "micro" size in early life. The micro size of prenidial infants makes them particularly amenable to microfabricated (IMT) systems and devices. Human eggs are spherical in shape. Eggs obtained from stimulated ovarian cycles will need to be matured if they are not quite ready for fertilization. Using unfertilized eggs obtained from stimulated ovarian cycles and matured in vitro under specific conditions before being fertilized, Roux et al. reported the morphometric (body size) parameters of human embryos in earliest development after being created by in vitro fertilization as being 157.4 microns for the outer diameter of the egg, 17.9 microns for the thickness of the shell, and 121.8 microns for the inner diameter of the egg which bounds the cells of the infant's body inside. However, these parameters can vary somewhat based on physical differences, maternal condition (e.g., increased age or smoking exposure has been associated with increased shell thickness), and the way unfertilized eggs arrive at maturity (i.e., naturally versus artificially) before fertilization. Note that at fertilization eggshells 10–20 microns thick with 120–140 micron outer diameters (100 micron inner diameters) are commonly reported. 100 microns is one-tenth of a millimeter. Composed of a protein matrix, not cells, the eggshell is often referred to as the zona pellucida (Latin for "clear zone") because it is translucent under the microscope. The embryo will expand inside the egg near hatching time and the shell will become thinner. The baby uses specialized shell-breaker cells to make a hole in the shell and then squeezes through. The baby leaves an empty shell behind after hatching. By the time a hatchling is ready to implant, the entire body of the infant may measure as much as half a millimeter in total diameter. Hatchlings require special care because they can invade or breach structures and become attached, lodged, or lost; also, their body tissues are directly exposed. Thus, systems and devices engineered for prenidial infants must take into account various morphological, physiological, and behavioral parameters and tolerances.

Cecchi et al. (U.S. Pat. No. 6,448,069) teach a picket fence structure comprising posts to keep babies separated from one another in a communal setting while in their eggs. Their particular picket fence structure is characterized with hindsight in view of the present teaching as a type of microcradle in array form. They teach the advantage that communal life provides a mutual contribution of beneficial endogenous substances, and that the picket fence structure keeps the babies separated for track-keeping purposes. See FIGS. 3A–C. But even though their picket fence structure is in effect a type of a microcradle in array form, it is not characterized as a vented microcradle because they do not incorporate a ventilation system with their structure for the purpose of fluidic ventilation.

In discussion with me, Kim et al. have suggested adaptation of their microcage structure to form a microcradle in the context of μICU objectives. The microcage is fabricated using an IMT technology called surface micromachining. Referring to FIGS. 4A B, the microcage has the appearance of a sea anemone and opens and closes under the action of pneumatic pressure applied to a diaphragm under the cage. However, further development is needed to reduce the size of the microcage so that it can cradle a baby at conception.

Sadly, unimaginative reliance on crude petri dish practices has persisted in the field of in vitro fertilization; according to such practices, prenidial infants are left at the bottom of an ordinary petri dish without any type of cradle or support whatsoever, without any fluidic ventilation, and without a proper understanding of thermoregulation; the children are treated like lab specimens rather than as patients. Such practices are incompetent and in my experience those responsible have no wish to change.

In an effort to advance diplomatic regard for the rights of prenids as patients in medicine, my institution, Juridic Embassy, has sponsored new progress in fertility care. As a consequence of my research in this area, I initiated the Micro ICU Project in response to the general lack of care being provided to children created by in vitro fertilization. The synergy of the project was created by the needs of the children in light of impressive new engineering technologies, particularly MEMS. Using IMT technologies such as MEMS, complementary metal oxide semiconductor technology (CMOS), and microfluidics, as well as various large-scale technologies, the goal of the project is to perfect an elaborately engineered patient care environment for children in prenidial incubators. An engineered provision of this sophistication for human embryos and hatchlings is called a micro intensive care unit (micro ICU, μICU, μ-ICU).

One objective of the Micro ICU Project is to provide a means to cradle and ventilate a prenidial infant. This objective provides the subject matter of my present invention.

3. Statement of the Necessity

For a neonatal incubator, the cradle portion of the incubator must allow for easy access to a patient while at the same time affording proper thermoregulation and ventilation at all times. A well-designed prenidial incubator should offer the same advantages.

What is needed is a vented microcradle for a prenidial incubator.

BRIEF SUMMARY OF THE INVENTION

According to my present invention, I teach a combination of a microcradle with a microfluidic ventilation system to accommodate associated microfluidics so as to provide a prenidial infant with gentle fluidic ventilation in a prenidial incubator. According to the invention, the microcradle portion of the incubator allows for easy access to a patient while at the same time affording proper thermoregulation and ventilation at all times. A vented microcradle according to the invention forms the central structure in a prenidial incubator environment.

Referring to FIG. 5, my invention is a vented microcradle 4 comprising a microfabricated enclosure designed to maintain a human embryo or hatchling (that is to say, a prenidial infant) P ("P" is for prenid) in a controlled care environment, the enclosure forming a cradle support for the human embryo or hatchling P and having a microfluidic ventilation system to provide the human embryo or hatchling P with gentle fluidic ventilation via associated microfluidics (not shown in this figure). In a preferred embodiment, the microfabricated enclosure is a picket fence structure 5 with a vented flooring 6; the vented flooring 6, which has a grill pattern, forms part of the ventilation system in connection with associated microfluidics. In operation, fluidic ventilation is provided by urging a fluid though the vented flooring 6 via associated microfluidics. The vented flooring 6 serves as a ventilation port for the ventilation system.

Unlike the present invention, the prior art does not teach or fairly suggest combination of a microcradle with a microfluidic ventilation system to accommodate associated microfluidics so as to provide a prenidial infant with gentle fluidic ventilation. Also, unlike a microcradle, a well-in-tank or channel structure does not admit easy access. As shown in FIG. 6 for the art of Beebe et al., a channel-type structure allows only difficult access. As shown in FIG. 1 for the art of Thompson et al., their well-type structure does not allow for access at an angle which is nearly parallel to a floor on which a prenid P rests, being that accessing equipment must be reached down into the well 1 via a tank 3. In contrast, as shown in FIG. 7, a microcradle 7 allows for a prenid P to be approached easily from the sides and from above. Yet although Cecchi et al. show what the present teaching would characterize in retrospect as a type of microcradle in array form, unlike the present invention they do not teach a vented microcradle.

These and other features and advantages of the present invention will be appreciated in the detailed description to follow.

DETAILED DESCRIPTION OF THE INVENTION

My invention is a combination of a microcradle with a microfluidic ventilation system to accommodate associated microfluidics so as to provide a prenidial infant with gentle fluidic ventilation, in other words, a vented microcradle. According to my invention, a vented microcradle comprises a microfabricated enclosure designed to maintain a human embryo or hatchling in a controlled care environment, the enclosure forming a cradle support for the human embryo or hatchling and having a microfluidic ventilation system to provide the human embryo or hatchling with gentle fluidic ventilation via associated microfluidics.

Figure 1:
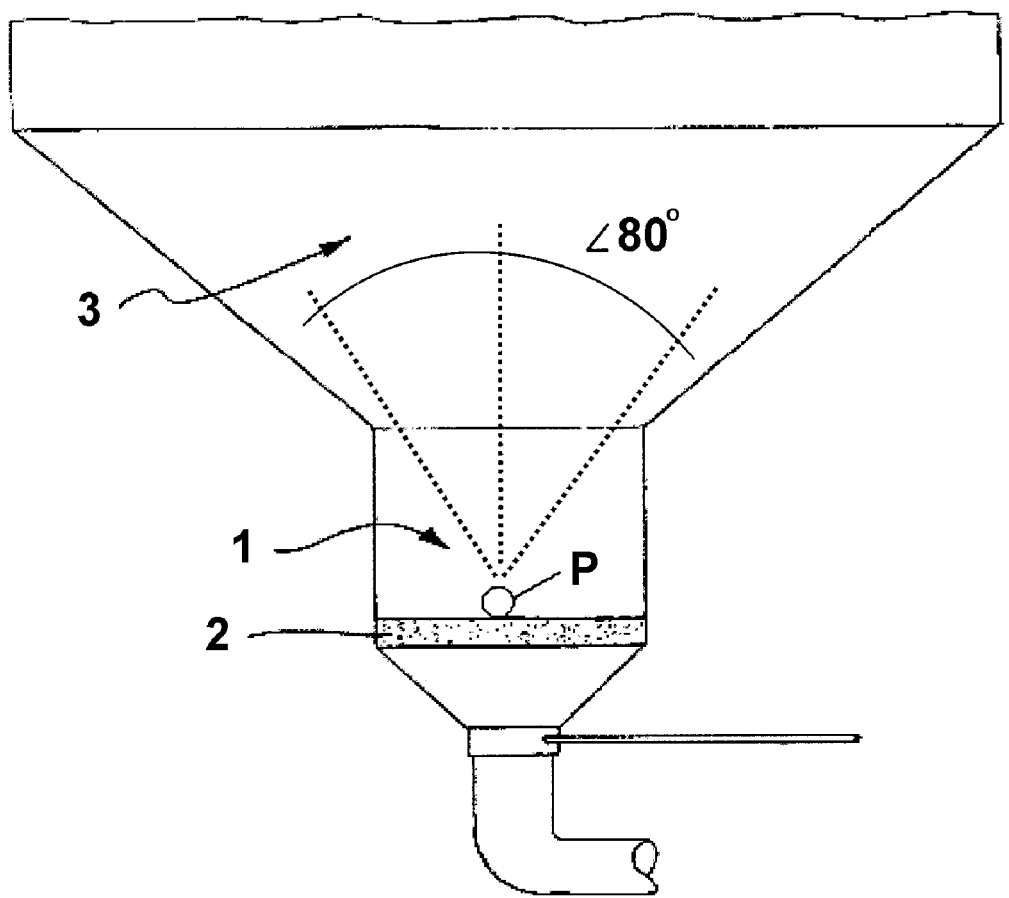
FIG. 1 is a schematic illustration of a portion of a prior art "embryo growth tank" having a well-in-tank type housing according to Thompson et al.; this figure also illustrates limited access to such a well-type housing.
Figure 2:
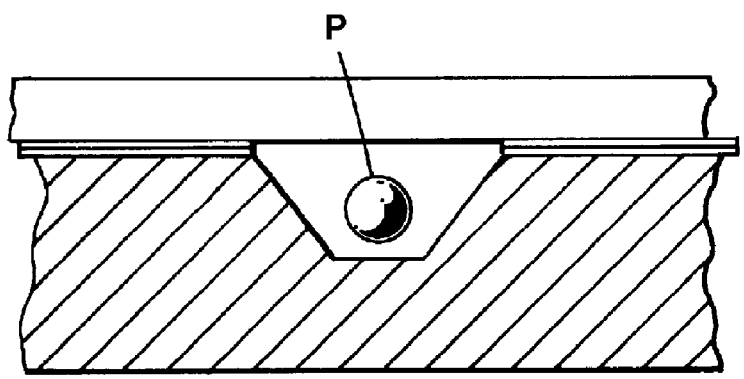
FIG. 2 is a longitudinal cross-sectional view of a prior art "microfluidic embryo handling device" having a channel-type housing according to Beebe et al.
Figure 3A:
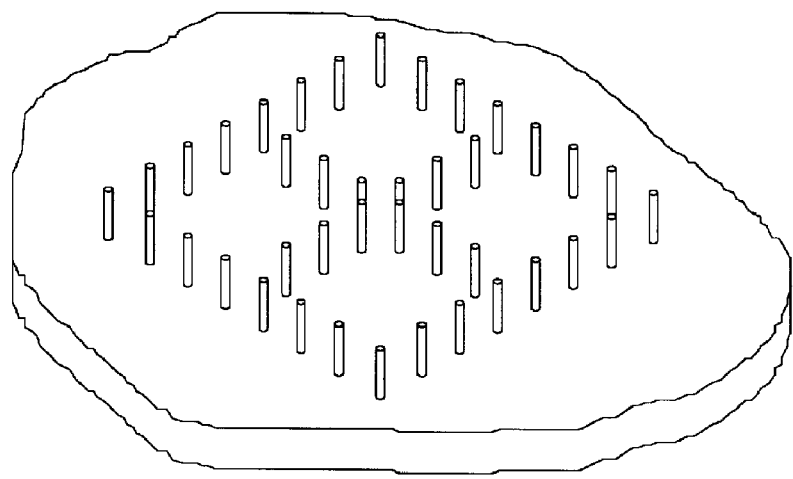
FIGS. 3A C are an enlarged fragmented perspective view, a plan view, and a side elevational view of a prior art compartmentalized structure according to Cecchi et al., which is characterized by the present teaching in retrospect as a type of microcradle in array form.
Figure 3B:
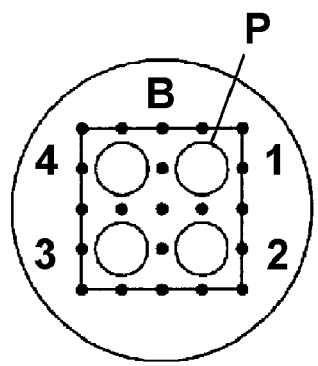
Figure 3C:
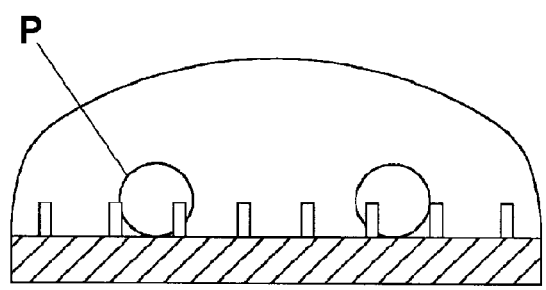
Figure 4A:
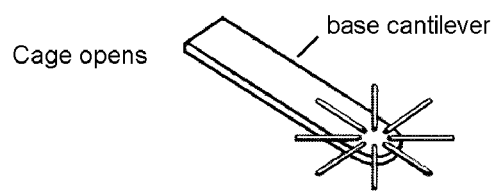
FIGS. 4A–B are perspective views of a prior art microcage according to Kim et al.
Figure 4B:
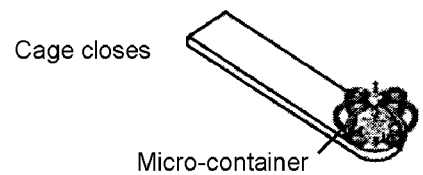
Figure 5:
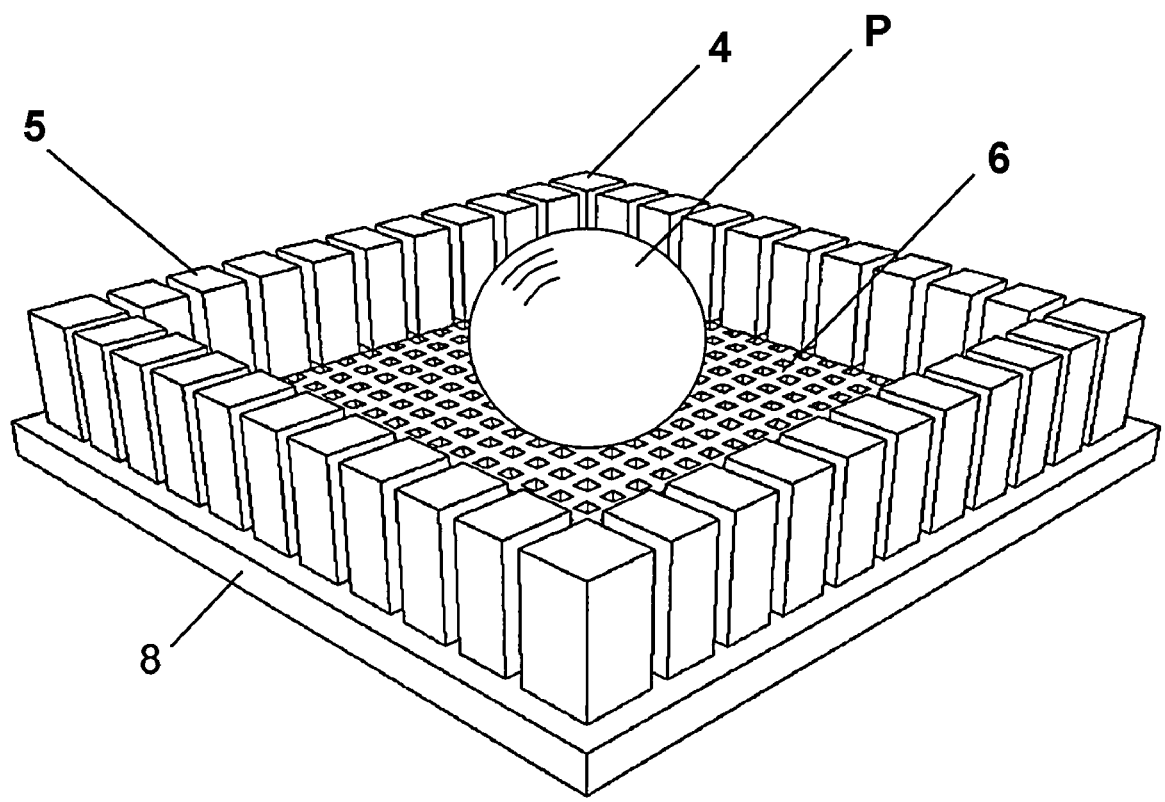
FIG. 5 is a perspective view of a vented microcradle according to the invention.
Figure 6:
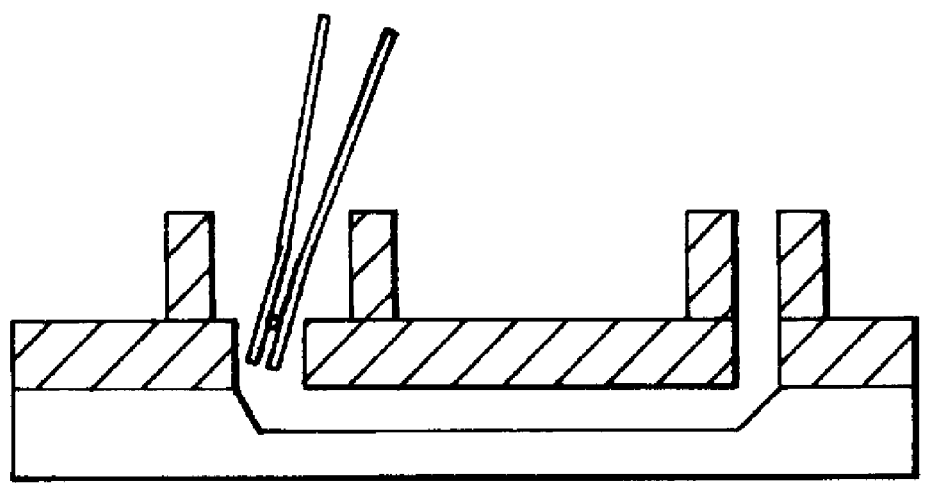
FIG. 6 is a longitudinal cross-sectional view of a prior art "microfluidic embryo handling device" according to the art of Beebe et al., illustrating limited access to a channel-type housing.
Figure 7:
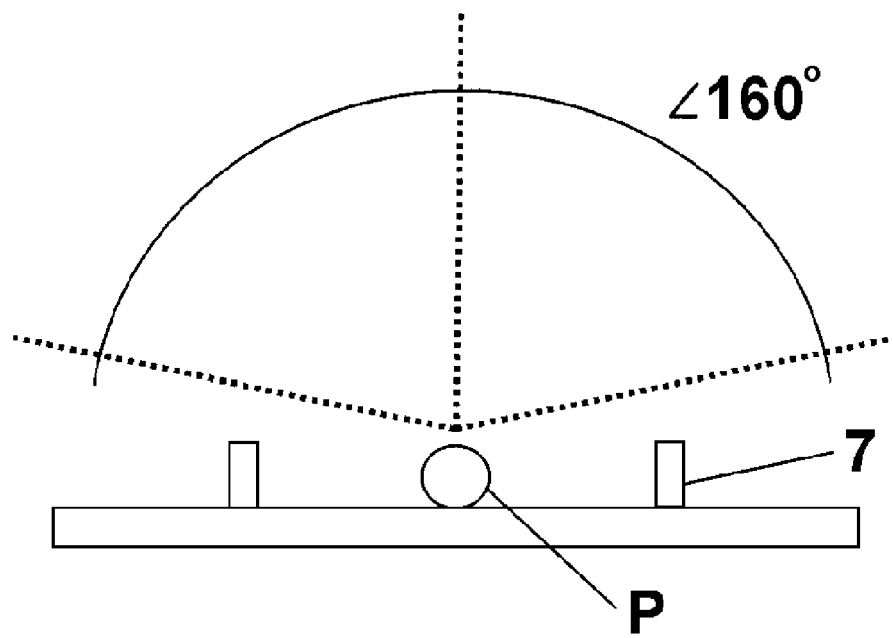
FIG. 7 is a longitudinal cross-sectional view of a microcradle illustrating easy access.
Figure 8:
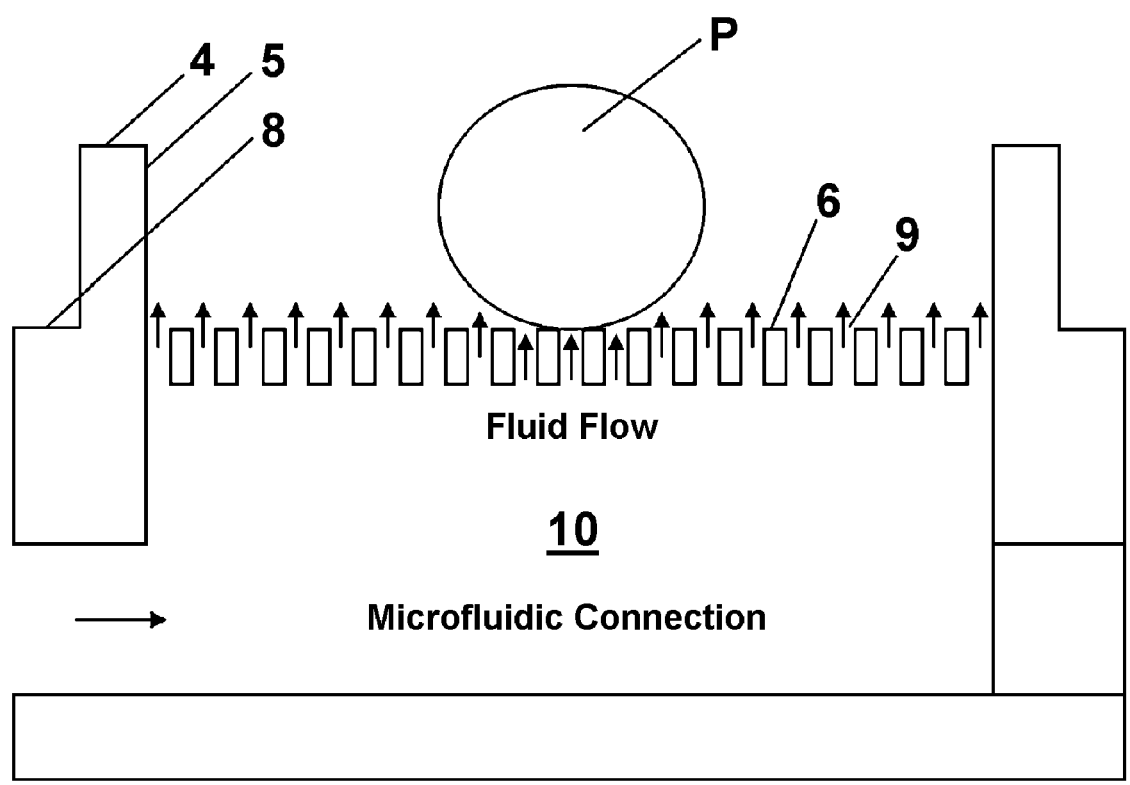
FIG. 8 is a longitudinal cross-sectional view of a vented microcradle according to the invention; this figure is most descriptive of the invention; and, FIG. 9 is a perspective view of an alternate embodiment of a vented microcradle according to the invention.

Referring to FIGS. 5 and 8, in a preferred embodiment of a vented microcradle 4 the microfabricated enclosure comprises a picket fence structure 5 with a vented flooring 6; the vented flooring 6 has a grill pattern of openings or vias 9 to permit passage of fluid therethrough in the manner of a grate or grating while at the same time blocking transit of a human embryo or hatchling P through the vented flooring 6; the vented microcradle 4 is flush with a supporting substrate 8; in operation, a microfluidic connection 10 is made beneath the vented flooring 6 and fluid is urged through the vented flooring 6 in conjunction with associated microfluidics so as to provide a prenidial infant P with gentle fluidic ventilation while cradled in the vented microcradle. The associated microfluidics may include channels, valves, reservoirs, and pumps for fluid as well as sensing and conditioning devices. A micropump is preferably employed to urge fluid to flow through the vented flooring 6; also, fluid pressure from a fluid reservoir may be employed to serve the same purpose. The vented flooring 6 serves as a ventilation port for the ventilation system.

Figure 9:
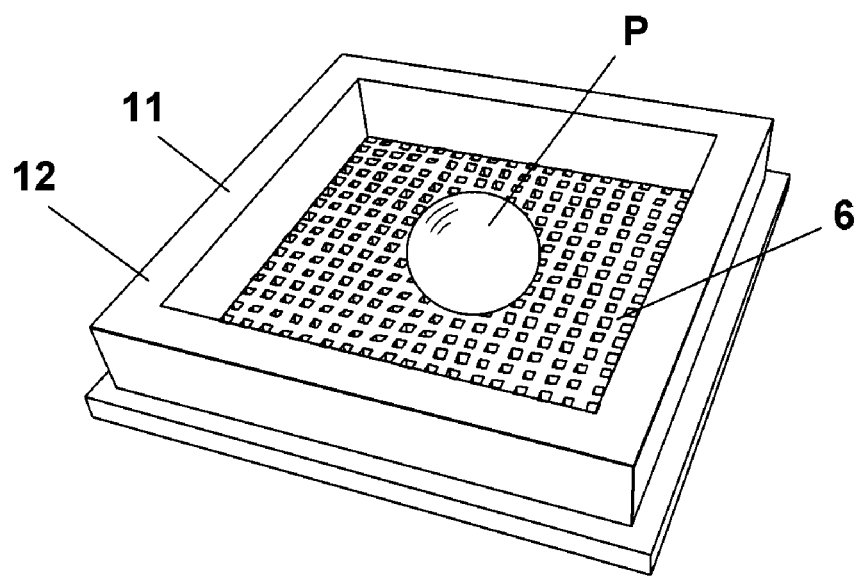

Referring to FIG. 9, in an alternate embodiment of a vented microcradle 11 the microfabricated enclosure comprises a wall structure 12 in place of a picket fence structure. In general, it is contemplated that various openings, sensors, systems, devices, or the like may be incorporated in the wall structure 12, in the vented flooring 6, or in the periphery of a vented microcradle.

In the preferred embodiment, a vented microcradle is manufactured in a glass substrate using any combination of chemical etching, laser etching, and ion beam etching; the vented microcradle is preferably formed at the center of a glassware container which also serves as the substrate; for example, etching may be done at the bottom of a glassware container such as a small petri dish; in turn, the glassware provides a containment reservoir for fluid in which a prenidial infant who is cradled inside the vented microcradle is kept submerged; use of the bottom of a containment reservoir as the substrate for manufacturing a vented microcradle obviates the need to bond or otherwise join the microcradle to the reservoir. The preference for glass etching over other microfabrication technologies is simply that little research has been done on the harmfulness to human prenidial infants of the materials and processing techniques employed in IMT technologies other than glass; for example, if a vented flooring is etched in silicon and a picket fence structure is made by depositing platinum or gold, chemicals used to etch the silicon may leach out of the silicon, and the presence of gold or platinum may have electrical implications for sensing equipment that are unfavorable. In contrast, glass, as well as glass manufacturing and processing steps, are known to be relatively inert and unharmful. There are a growing number of skilled artisans in the private sector and at academic and government institutions capable of manufacturing a vented microcradle in the preferred embodiment along with microfluidic systems and devices of a relevant kind. In the private sector, Precision Microfab, LLC (Arnold, Md.) is capable of manufacturing the preferred embodiment in glass using technology from the field of laser precision microfabrication (laser etching).

In operation, fluid is urged through the vented flooring 6 so as to provide fluidic ventilation for a prenidial infant P who is cradled in the vented microcradle. In one mode of operation, shown in FIG. 8, fluid is made to flow in the upward direction through the vented flooring 6; this has the advantage of reducing the risk that the vented flooring 6 will become clogged by debris. In another mode of operation, fluid is made to flow in the downward direction.

In yet another mode of operation, fluid is made to flow to-and-fro through the vented flooring 6, in likeness to the beating of cilia along the lumen of the fallopian tube, but in such a way that a net movement of fluid is created in a given direction over time, for example in the upward direction; net movement is needed to prevent the fluid from getting stale, that is to say, from accumulating too many wastes and from being depleted in resources; yet the to-and-fro movement provides circulation while at the same time maintaining a concentration of endogenous substances produced by the infant that may be conducive to the infant's health and which might otherwise be whisked away too soon by continuous flow in one direction; the to-and-fro movement of fluid may be urged by a reversible pump or by a valve that switches between positive and negative channels of fluid pressure created either by oppositely pressurized reservoirs or by oppositely oriented pumps or by any oppositely oriented combination of a reservoir and a pump. In yet another mode of operation, somewhat similar in principle to the to-and-fro mode described above, a short path of fluid is made to recirculate, with the fluid being refreshed periodically or in continuous proportion to prevent staleness. In general, fluid recirculation may be accomplished via ventilation ports for fluid entry and exit via the floor, sides, or from above the microfabricated enclosure, or via the containment reservoir in which the vented microcradle is submerged.

A complex system of channels, valves, reservoirs, and pumps can be included with the microfluidics of the vented microcradle. It goes without saying that microfluidic communication can be established according to the art between the microfluidic connection 10 beneath the vented flooring 6 of a vented microcradle and another fluid path or channel to the containment reservoir in which the vented microcradle is submerged. Also, a micropipette can be used to deliver or drip medication from above the patient, while a micropump draws fluid through the vented flooring and exits the fluid through a selected exit port. A micropipette can also be used from above and aside the patient to vacuum debris for the sake of hygiene or to free a clogged portion of the vented flooring. Nanocoatings, that is to say, coatings devised by nanotechnology, may be employed in conjunction with the microfluidics and ventilation system of a vented microcradle to improve fluid flow by making surfaces slipperier.

It may be noted in general that micropipettes, with or without the aid of microstructures to prevent transit of the patient under the action of fluid flow, can be used to provide crude fluidic ventilation. The micropipettes may be arranged in single, plural, or assembly form. Although simple, unlike a vented microcradle, micropipette arrangements require micromanipulators for placement and thus can get in the way; moreover, repeatable parameters of fluid flow may not be as easy to establish with micropipettes as with a vented microcradle.

Hatching is an early human behavior, observable when an embryo breaches the eggshell. Note that surgically assisted hatching, in which holes are surgically made in the eggshell in anticipation of hatching, confirms the animated nature of the hatching behavior since an exit based on a pressure mechanism would be impossible when multiple holes are made present in the shell. This understanding should be clear from the standpoint of biophysics, for notably the embryo would be unable to prefer one hole over another based on a pressure mechanism, and even so back pressure would escape through an opposing hole, thus making it impossible to hatch without involving actual movement. Consequently, hatching is correctly understood as a human behavior involving a type of movement. The ability for movement is not surprising, since it is well known that the ultimate basis for biological movement is contained within cells in the form of chemical contractions exerted upon a cell's cytoskeleton.

The parameters and abilities of the breaching behavior associated with the human hatching event are not fully understood. Of special concern in the design of a vented microcradle is the prospect that the baby might hatch and subsequently breach either the microcradle or an associated system such as the ventilation system. Holes in the shell 10 microns in diameter are easily breached, but this entails substantial stretching of the hole as the baby escapes. It is assumed that long, rigid channels of small diameter would be impossible to breach. However, there is also concern that the baby might get partially stuck or dangerously attached with respect to a hole or channel that can be partially invaded.

Thus, an important consideration in the design of a microcradle is that the structure be breach guarded. There is also a therapeutic prospect of placing structures with breachable apertures or spaces within a care environment, such as within the enclosure of a microcradle, so as to enable a hatchling infant to repeat his or her breaching behavior for exercise by going through the breachable structures in a safe way. The structures should be able to be opened or released in case the baby gets tired or stuck. It may be noted that breaching is not of such a concern if it is certain that transfer will occur well before hatching time. It may also be noted that hatching is an intelligent behavior. Although it was once thought that differentiated neurons are needed for intelligence, it is now realized in view of the hatching behavior and our understanding of molecular computing, which stems from our knowledge of the new field of nanotechnology, that "brain power" actually resides within cells in the form of molecular computing, whereas the distinction of the differentiated neuron is simply its elaboration as an interconnect. Therefore, in respect of a baby's intelligence and behavioral capabilities during prenidial development, it is important from a therapeutic perspective to ensure that the microcradle environment is not "too boring" for the baby to handle.

Because competent thermoregulation is needed for competent prenidial incubation, it is essential for any system or device used in a prenidial incubator to be compatible with application of my teaching in U.S. Pat. No. 6,694,175. In view of that teaching in combination with the present teaching, a quantum well infrared photodetector (QWIP) camera can be fitted with a microscope lens and placed above the infant who is kept within a vented microcradle; or the QWIP camera can be incorporated with a microscope or fiber optics system; or another suitable temperature detection technology can be employed according to the art. To warm the infant in the manner of a heat lamp, infrared light emitting diodes (IR LED's) can be focused on the patient from the sides or from above, or they may even be incorporated in the microcradle structure itself or its proximity. It is understood according to the art that the fluid incubation medium is kept slightly cool to provide a thermal gradient for heat dissipation and to prevent the patient from getting too warm, and that the heat lamps provide fine controls to offset the ambient coolness of the fluid incubation medium.

Alternate or additional means of heating and cooling the baby can be employed in tandem with the microfluidics of the vented microcradle. Such means can be employed as a substitute for the heat lamps or in tandem with the heat lamps to provide controls of intermediate fineness. For example, fluid urged upward through the microcradle to ventilate the baby can be preheated; one means is to mix hot and cold fluid media using a valve controlled by feedback from the QWIP camera which also detects the temperature of the emerging fluid; another means is to heat or cool the fluid directly; pretesting of the fluid temperature can be done in either case, and then refined determination can be made using the QWIP camera so that fine temperature adjustments can be made by feedback control.

It may be noted that various sensing devices, including an infrared camera used to detect the patient's temperature, can be used to acquire feedback as to the effect on the patient's health and metabolism of the fluid flow and fluid content to which the patient is exposed in a vented microcradle. Thus, the effects of fluid flow and content on patient health and metabolism may be appreciated by thermal image and other sensing methods so that feedback controls may be obtained (e.g., to regulate the rate of fluid flow experienced by the patient). Feedback may be similarly obtained regarding patient status in general, including with respect to various treatments, operations, or events. It is important that thermal signatures of various devices or systems do not interfere with the thermal image gathered for the patient.

Although the preferred embodiment employs a vented flooring, fluidic ventilation could also be provided in a vented microcradle from the sides or even from above. By gentle fluidic ventilation is meant that it is anticipated that fluid flow rates should generally not exceed 1 to 10 micrometers per second through the vented flooring 6. Referring to FIGS. 5 and 8, typical dimensions for a vented microcradle according to the preferred embodiment are as follows: vias 9 in the vented flooring 6 are 10 microns wide and 30 or more microns deep; pickets in the picket fence structure 5 are 80–500 microns in height, 30 microns wide, and 40 microns deep with pickets spaced 10 microns apart; the grill pattern of the vented flooring 6 may pack vias 9 cubically as shown or hexagonally for example, with 10 micron spacing; the inner dimensions of the vented microcradle may be 370 microns by 370 microns square as shown, although circular, oval, or other shapes are possible. Larger inner dimensions may be provided as needed, for example, to accommodate the expansion and growth of infants more than three days old, to make room for hatching infants, to facilitate removal of the empty shell after hatching, or to facilitate other actions performed for the benefit of the patient. Note that according to the art of microfluidics more pressure is required to urge fluid through a via of a small diameter (small channel width) and long depth (long channel length) and that too much pressure may compromise the structural integrity of the vented flooring. Depending on the material used, structural integrity may also be compromised if openings or vias are spaced too close together or if the vented flooring is too thin. Though it is contemplated that, for example, vias 10 microns wide and 30 microns deep will prevent breaching, or that wider or shallower ones may suffice, the depth may need to be increased and the width narrowed upon further study; also, research is contemplated relating to shapes and coatings for openings/surfaces so as to inhibit breaching, invasion, or adhesion. Breaching, invasion, and adhesion are not a design consideration in cases where embryos are to be transferred before hatching time; in such a case, for example, openings may be comparatively widened.

According to the figures above, at a maximum flow rate of 10 microns per second through a vented flooring 370 by 370 microns square, a vented microcradle would have a fluid output of 1.4 nanoliters per second, or about two eyedropper-size drops worth of fluid per day. A flow rate of 0.1 microns per second corresponds to a fluid output of 14 picoliters per second. Microfluidic flow meters and micropumps are available in both integrated and discrete form to handle flows in the range of picoliters to nanoliters per second. These exemplary calculations emphasize the extreme subtlety of the claimed device.

It may be noted that when the preferred embodiment is etched in glass, a well is etched around the vented microcradle to a depth at least equal to the height of the microfabricated enclosure. But when employing a solid wall structure 12 as shown in the FIG. 9 embodiment, then when etched in glass, the wall can simply be formed by the substrate, so that the vented flooring 6 in effect rests in a shallow, open well equal in depth to the height of the wall; but unlike various covered well or well-in-tank structures proposed by Beebe et al. and Thompson et al., a vented microcradle structure allows for easy access to a patient while maintaining fluidic ventilation at all times. Unlike prior art well or channel type housings, because a microcradle according to the present invention admits easy access to the prenidial patient contained therein, various medical treatments, surgery, hygiene administration, and other forms of care and handling are easier to perform on the patient. Importantly, unlike prior art ventilated housings for a prenidial infant in which fluid flow is maintained via pressure in a tank in which the housing is kept (e.g., Thompson et al.) or by a covered channel or well which serves as the housing (e.g., Beebe et al.), with a vented microcradle the fluid flow does not need to cease while treatments or other actions are being performed because an open type housing is provided in association with microfluidics, in contrast to a closed type housing. In other words, unlike the art of Thompson et al. and Beebe et al., the present invention enables fluid flow through the ventilation system of a vented microcradle to be maintained continuously, even while the patient is being directly accessed inside the enclosure. In contrast, with the art of Thompson et al. the rate of fluid flow is related to pressure in the tank, and so the rate of fluid flow will change when the tank is opened to allow access to an embryo; and, with the art of Beebe et al., as shown for their FIGS. 5A–C and 6B, detailed beginning at column 5, line 62, fluid flowing in a channel or compartment would interfere with access to an embryo contained therein, since positioning of the embryo and removal of fluid are required to access the embryo by micropipette or other instrument via an access hole or well. In contrast, the present invention provides an easy-access microcradle that continuously affords proper ventilation. So, unlike the cumbersome ventilated housings of the prior art, a vented microcradle provides an unencumbered housing for a prenidial infant that affords proper ventilation at all times.

A vented microcradle employs a microfabricated grill pattern of vias 9 in a vented flooring 6 to fluidically ventilate a patient, whereas Thompson et al. employ a microporous filter 2. Thompson et al do not teach a pattern or regularity of pores for their microporous filter; they also do not teach a use of microfabrication technology to produce such a filter, implying that the pores in their filter take on a random pattern as is known to be the case for microporous filters that are not produced by microfabrication. An advantage of a microfabricated grill pattern is that the parameters of fluid flow are well defined (i.e., laminar flow) due to the regular structure of the grill pattern and the nature of microfluidics; thus, the parameters of fluid flow are more repeatable according to the present invention than is provided by the somewhat random structure associated with a microporous filter. Well-defined parameters of fluid flow are especially important if fluid is to be pulsed to-and-fro since this ensures that fluid will flow evenly when forced through a ventilation structure such as the vented flooring 6; in contrast, random variation in a microporous filter type structure might cause fluid flow to be focused at unpredictable places along the surface of the microporous filter 2 structure, making it difficult to assess the amount of flow being actually experienced by the patient. The issue of controlled fluid flow is especially important in that the microfluidics associated with the vented microcradle can also be used to deliver medications or other fluidic treatments in the upward (inward) direction of flow, and conversely, in the downward (outward) direction of flow, microfluidics can be used to channel fluid from the vicinity of the patient to devices where the condition or content of the fluid can be sensed by one or more sensing devices; thus, it is important that the parameters of fluid flow be dependable so that such processes may be conducted with accuracy. Notably, withdrawing fluid from around the patient for sensing is important for monitoring health and conditions and can be accommodated by the microfluidic system associated with a vented microcradle; this feature is especially important because individual sensors will oftentimes be difficult to fabricate and place in direct proximity to the patient, making remote location and hence fluid transport thereto necessary. Channeling fluid quantities via the (main) ventilation system will give better exposure to the patient who rests on the flooring (bed) of the microcradle. However, separate microfluidic channels, or even micropipettes, can also be employed to channel fluid quantities directly to and from the enclosure of a vented microcradle in a way independent of the main ventilation system.

In view of this disclosure, a vented microcradle according to the present invention should be regarded as a high quality structure that is essential for sophisticated prenidial infant care in an incubator setting. A vented microcradle according to the present invention, as will be appreciated by those skilled in IMT arts, can be micromanufactured by a number of different IMT processes and in any variety of configurations, including arrays. It is contemplated that the advantages of a vented microcradle will have been made so obvious by the present teaching that practitioners of prenidial medicine will appreciate that a vented microcradle is indispensable in the context of prenidial incubation.

Finally, it is contemplated that new and useful configurations for a vented microcradle will need to be devised over time to suit changing architectures for the micro intensive care unit environment as a whole, particularly as multiple systems and devices become integrated in intimate proximity to the infant. For this reason, the field of vented microcradle design for prenidial incubators should be interpreted as a crowded art, because it is foreseen that inventions will be needed in the future with claims taking the form: "A new and useful configuration for a vented microcradle, comprising:"

What is claimed is:

1. A vented microcradle comprising a microfabricated enclosure designed to maintain a human embryo or hatchling in a controlled environment for medical care, the enclosure, having a flooring surrounded by a wall structure with an open top and having a ventilation port in the flooring or wall comprising a microfabricated grill pattern of openings to permit flow in and out of the enclosure, forming a cradle support for the human embryo or hatchling and having a microfluidic ventilation system connected to the ventilation port including means for selectably providing a flow in, out, or to and fro through the ventilation port, to provide the human embryo or hatchling with gentle, fluidic ventilation via associated microfluidics.

2. The vented microcradle of claim 1 wherein the ventilation system includes connections, channels, valves, reservoirs, and pumps to urge fluid through the ventilation system to ventilate the human embryo or hatchling within the enclosure.

3. The vented microcradle of claim 2 wherein flow is controlled in reference to feedback provided by means of thermal images or measurements taken of an actual body temperature of the human embryo or hatchling within the enclosure and which said actual body temperature can differ from an ambient temperature of a fluid incubation medium.

4. The vented microcradle of claim 2 wherein the ventilation system further includes means to deliver and withdraw medications and other fluidic treatments.

5. The vented microcradle of claim 1 further including means to monitor and maintain the controlled environment and patient health or status within the enclosure.

6. The vented microcradle of claim 1 wherein the wall structure comprises a picket fence structure.

7. The vented microcradle of claim 1 wherein the enclosure further includes a plurality of ventilation ports.

8. The microfluidic ventilation system of claim 1 wherein the enclosure is made by etching in a glass containment reservoir.

9. The vented microcradle of claim 1 further including intimate integration with a device or system selected from the group consisting of microfluidics, openings, sensors, light emitting diodes, fiber optics, cameras or imagers, structures with breachable apertures or spaces, medical or surgical units, thermal or chemical conditioning units, hygiene administration units, feedback control devices and systems, and means for thermoregulating a patient, whereby the vented microcradle forms a central structure in a prenidial incubator environment and accepts intimate combination with other patient care devices and systems.

10. A vented microcradle comprising a microfabricated glass enclosure designed to maintain a human embryo or hatchling in a controlled environment for medical care, the enclosure, having a vented flooring comprising a grill pattern of openings surrounded by a wall structure, the wall structure including openings that are evenly spaced to form a picket fence structure, forming a cradle support for the human embryo or hatchling and having a microfluidic ventilation system connected to the vented flooring including means for providing a flow to and fro through the vented flooring in likeness to the beating of cilia along the lumen of the fallopian tube, to provide the human embryo or hatchling with gentle, fluidic ventilation via associated microfluidics.

11. The vented microcradle of claim 10 wherein the ventilation system includes connections, channels, valves, reservoirs, and pumps to urge fluid through the ventilation system to ventilate the human embryo or hatchling within the enclosure.

12. The vented microcradle of claim 11 wherein flow is controlled in reference to feedback provided by means of thermal images or measurements taken of an actual body temperature of the human embryo or hatchling within the enclosure and which said actual body temperature can differ from an ambient temperature of a fluid incubation medium.

13. The vented microcradle of claim 11 wherein the ventilation system further includes means to deliver and withdraw medications and other fluidic treatments.

14. The vented microcradle of claim 10 further including means to monitor and maintain the controlled environment and patient health or status within the enclosure.

15. The vented microcradle of claim 10 further including intimate integration with a device or system selected from the group consisting of microfluidics, openings, sensors, light emitting diodes, fiber optics, cameras or imagers, structures with breachable apertures or spaces, medical or surgical units, thermal or chemical conditioning units, hygiene administration units, feedback control devices and systems, and means for thermoregulating a patient, whereby the vented microcradle forms a central structure in a prenidial incubator environment and accepts intimate combination with other patient care devices and systems.

16. A microfluidic ventilation system comprising a vented flooring connected to a microfluidic system designed to ventilate a human embryo or hatchling in a controlled environment for medical care, the vented flooring, comprising a microfabricated grill pattern of openings in a supporting substrate, forming a resting support for the human embryo or hatchling and having a microfluidic connection underneath to establish fluidic communication between the vented flooring and the microfluidic system, the microfluidic system including means for selectably providing a flow in, out, or to and fro through the vented flooring, to provide the human embryo or hatchling with gentle, fluidic ventilation via associated microfluidics.

17. The microfluidic ventilation system of claim 16 wherein the ventilation system includes connections, channels, valves, reservoirs, and pumps to urge fluid through the ventilation system to ventilate the human embryo or hatchling within the enclosure.

18. The microfluidic ventilation system of claim 17 wherein flow is controlled in reference to feedback provided by means of thermal images or measurements taken of an actual body temperature of the human embryo or hatchling on top of the resting support and which said actual body temperature can differ from an ambient temperature of a fluid incubation medium.

19. The microfluidic ventilation system of claim 17 wherein the ventilation system further includes means to deliver and withdraw medications and other fluidic treatments.

20. The microfluidic ventilation system of claim 16 further including means to monitor and maintain the controlled environment and patient health or status on top of the resting support.

21. The microfluidic ventilation system of claim 16 wherein the supporting substrate is made of glass.

22. The microfluidic ventilation system of claim 16 further including intimate integration with a device or system selected from the group consisting of microfluidics, openings, sensors, light emitting diodes, fiber optics, cameras or imagers, structures with breachable apertures or spaces, medical or surgical units, thermal or chemical conditioning units, hygiene administration units, feedback control devices and systems, and means for thermoregulating a patient, whereby the vented flooring forms the central resting support in a prenidial incubator environment and accepts intimate combination with other patient care devices and systems.

* * * * *